United States Patent [19]

Yang et al.

[11] Patent Number: 5,124,005
[45] Date of Patent: * Jun. 23, 1992

[54] SEPARATION OF METHYLENE CHLORIDE FROM ETHYL VINYL ETHER BY EXTRACTIVE DISTILLATION

[75] Inventors: Lloyd Berg, 1314 S. Third Ave.,
Zuyin Yang, 805 Peter Koch Tower, both of Bozeman, Mont. 59715

[73] Assignee: Lloyd Berg, Bozeman, Mont.

[*] Notice: The portion of the term of this patent subsequent to Mar. 3, 2009 has been disclaimed.

[21] Appl. No.: 690,770

[22] Filed: Apr. 25, 1991

[51] Int. Cl.⁵ .................. B01D 3/40; C07C 17/38; C07C 43/16
[52] U.S. Cl. .................. 203/57; 203/58; 203/60; 203/62; 203/63; 203/64; 568/693; 570/262
[58] Field of Search .............. 203/60, 62, 64, 58, 203/63, 57; 570/262; 568/693, 687

[56] References Cited

U.S. PATENT DOCUMENTS

| | | | |
|---|---|---|---|
| 2,641,616 | 6/1953 | Ellinger | 568/693 |
| 2,779,720 | 1/1957 | Tanona | 568/693 |
| 3,878,058 | 4/1975 | Tanaka et al. | 568/693 |
| 4,036,703 | 7/1977 | Leroi et al. | 203/60 |
| 4,121,978 | 10/1978 | Becuwe | 203/60 |

FOREIGN PATENT DOCUMENTS

| | | | |
|---|---|---|---|
| 643135 | 6/1962 | Canada | 568/699 |
| 249870 | 12/1987 | European Pat. Off. | 568/699 |

*Primary Examiner*—Wilbur Bascomb, Jr.

[57] ABSTRACT

Methylene chloride cannot be completely separated from ethyl vinyl ether by conventional distillation or rectification because of the minimum boiling azeotrope. Methylene chloride can be readily separated from ethyl vinyl ether by extractive distillation. Typical effective agents are ethylene glycol methyl ether acetate, 2-hexanone and 1-nitropropane.

1 Claim, No Drawings

SEPARATION OF METHYLENE CHLORIDE FROM ETHYL VINYL ETHER BY EXTRACTIVE DISTILLATION

FIELD OF THE INVENTION

This invention relates to a method for separating methylene chloride from ethyl vinyl ether using ceratin organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Methylene chloride, B.P.=40° C. forms a minimum boiling azeotrope with ethyl vinyl ether, B.P.=33° C. at 31° C. containing 70% methylene chloride. The methylene chloride-ethyl vinyl ether azeotrope is impossible to separate by distillation because the relative volatility of an azeotrope is 1.0. Extractive distillation would be an attractive method of effecting the separation of methylene chloride from ethyl vinyl ether if agents can be found that (1) will enhance the relative volatility between methylene chloride and ethyl vinyl ether and (2) are easy to recover, that is, form no azeotrope with methylene chloride or ethyl vinyl ether and boil sufficiently above these compounds to make separation by rectification possible with only a few theoretical plates.

Extractive distillation typically requires the addition of an equal amount to twice as much extractive agent as the methylene chloride-ethyl vinyl ether on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the methylene chloride and the ethyl vinyl ether otherwise it will form a two phase azeotrope with it and some other method of separation will have to be employed.

TABLE 1

Effect of Relative Volatility on the Separation of Methylene Chloride From Ethyl Vinyl Ether at 99% Purity

| Relative Volatility | Theoretical Plates | Actual Plates, 75% Efficiency | Actual Plates, 75% Eff., Min. Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. When ordinary rectification is used, 87 actual plates of 75% efficiency are required at minimum reflux ratio to separate methylene chloride from ethyl vinyl ether in 99% purity. If extractive distillation is employed with an agent that converts the relative volatility to 1.7, only 29 actual plates are required.

OBJECTIVE OF THE INVENTION

The objects of this invention are to provide a process or method of azeotropic or extractive distillation that will enhance the relative volatility of methylene chloride to ethyl vinyl ether in their separation in a rectification column. It is a further object of this invention to identify organic compounds that are stable, can be separated from methylene chloride or ethyl vinyl ether by rectification with relatively few plates and can be recycled to the extractive distillation column with little decomposition.

SUMMARY OF THE INVENTION

The objects of this invention are provided by a process for the separation of methylene chloride from ethyl vinyl ether which entails the use of certain organic compounds as the agent in extractive distillation.

DETAILED DESCRIPTION OF THE INVENTION

We have discovered that certain organic compounds will effectively increase the relative volatility between methylene chloride and ethyl vinyl ether and permit the separation of methylene chloride from ethyl vinyl ether by rectification when employed as the agent in extractive distillation. Table 2 lists the agents that we have found to be effective. The data in Tables 2 and 3 was obtained in a vapor-liquid equilibrium still. In every case, the starting mixture was the methylene chloride-ethyl vinyl ether azeotrope. The relative volatilities are listed for each of the agents investigated. The compounds which are effective are methyl acetate, ethyl acetate, isopropyl acetate, n-propyl acetate, isobutyl acetate, n-butyl acetate, n-amyl acetate, vinyl acetate, methyl vinyl acetate, ethylene glycol methyl ether acetate, 3-hexanone, 3-pentanone, 4-methyl-2-pentanone, 3,3-dimethyl-2-butanone, 3-methyl-2-butanone, dioxane, 1,2-dimethoxypropane, methyl ethyl ketone, methyl vinyl ketone, 2-hexanone, 5-methyl-2-hexanone, methyl isoamyl ketone, ethyl butyl ketone, propylene glycol dimethyl ether, propylene glycol methyl ether, nitromethane, nitroethane, 1-nitropropane and 2-nitropropane.

Table 3 lists a number of compounds that proved to be ineffective as extractive distillation agents in the separation of methylene chloride from ethyl vinyl ether.

Ethylene glycol ethyl ether acetate whose relative volatility had been determined in the vapor-liquid equilibrium still was then evaluated in a glass perforated plate rectification column possessing 7.3 theoretical plates and the results listed in Tab;e 4. After an hour of continuous operation, a relative volatility of 1.65 was obtained with this extractive agent.

THE USEFULNESS OF THE INVENTION

The usefulness or utility of this invention can be demonstrated by referring to the data presented in Tables 2 and 4. All of the successful agents show that methylene chloride can be separated from ethyl vinyl ether by extractive distillation in a rectification column and that the ease of separation as measured by relative volatility is considerable,

TABLE 2

Effective Agents For Separating Methylene Chloride From Ethyl Vinyl Ether

| Compounds | Relative Volatility |
|---|---|
| Ethyl acetate | 1.5 |
| Isopropyl acetate | 1.45 |
| n-Propyl acetate | 1.5 |
| Isobutyl acetate | 1.45 |
| n-Butyl acetate | 1.35 |
| n-Amyl acetate | 1.3 |
| Vinyl acetate | 1.3 |
| Methyl vinyl acetate | 1.45 |
| Ethylene glycol methyl ether acetate | 1.9 |
| Methyl acetate | 2.0 |
| 3-Hexanone | 1.5 |
| 3-Pentanone | 1.4 |
| 4-Methyl-2-pentanone | 1.4 |
| 3,3-Dimethyl-2-butanone | 1.35 |
| 3-Methyl-2-butanone | 1.55 |
| 1,2-Dimethoxypropane | 1.6 |
| Dioxane | 1.85 |
| Methyl ethyl ketone | 1.65 |
| Methyl vinyl ketone | 1.8 |
| 2-Hexanone | 1.65 |
| 5-Methyl-2-hexanone | 1.4 |
| Methyl isoamyl ketone | 1.55 |
| Ethyl butyl ketone | 1.5 |
| Propylene glycol dimethyl ether | 1.75 |
| Propylene glycol methyl ether | 1.45 |
| Nitromethane | 1.3 |
| Nitroethane | 1.45 |
| 1-Nitropropane | 1.7 |
| 2-Nitropropane | 1.3 |

TABLE 3

Ineffective Agents

| 2,2-Methoxypropane | Ethylene glycol ethyl ether acetate |
| 3-Methyl-1-butanol | n-Butanol |
| Isobutanol | 2-Butanol |

TABLE 4

Data From Run Made In Rectification Column

| Agent | Column | Time hrs. | Weight % $CH_2Cl_2$ | Weight & EtVinEther | Relative Volatility |
|---|---|---|---|---|---|
| Ethylene glycol methyl ether acetate | Overhead | 1 | 90.3 | 9.7 | 1.65 |
| | Bottoms | | 19.7 | 80.3 | |

WORKING EXAMPLES

EXAMPLE 1

Eighty grams of the methylene chloride-ethyl vinyl ether azeotrope and 30 grams of ethylene glycol methyl ether acetate were charged to a vapor-liquid equilibrium still and refluxed for eleven hours. Analysis indicated a vapor composition of 35.2% methylene chloride, 64.8% ethyl vinyl ether; a liquid composition of 22.1% methylene chloride, 77.9% ethyl vinyl ether which is a relative volatility of methylene chloride to ethyl vinyl ether of 1.9.

EXAMPLE 2

A solution comprising 140 grams of methylene chloride and 60 grams of ethyl vinyl ether was placed in the stillpot of a 7.3 theoretical plate rectification column. When refluxing began, an extractive agent comprising ethylene glycol methyl ether acetate was pumped into the column at a rate of 15 ml/min. The temperature of the extractive agent as it entered the column was 65° C. After establishing the feed rate of the extractive agent, the heat input to the methylene chloride-ethyl vinyl ether in the stillpot was adjusted to give a total reflux rate of 40 ml/min. After an hour of operation at total reflux, the overhead and bottoms samples of approximately two ml. were collected and analysed. The overhead analysis was 90.3% methylene chloride, 9.7% ethyl vinyl ether and the bottoms analysis was 19.7% methylene chloride, 80.3% ethyl vinyl ether. This gives an average relative volatility of 1.65 for each theoretical plate. This data is presented in Table 4.

We claim:

1. A method for recovering methylene chloride from a mixture of methylene chloride and ethyl vinyl ether which comprises distilling a mixture of methylene chloride and ethyl vinyl ether in the presence of about one part of an extractive agent per part of methylene chloride-ethyl vinyl ether mixture, recovering methylene chloride as overhead product and obtaining the ethyl vinyl ether and the extractive agent from the stillpot, wherein said extractive agent consists of one material selected from the group consisting of methyl acetate, ethyl acetate, isopropyl acetate, n-propyl acetate, isobutyl acetate, n-butyl acetate, n-amyl acetate, vinyl acetate, methyl vinyl acetate, ethylene glycol methyl ether acetate, 3-hexanone, 3-pentanone, 4-methyl-2-pentanone, 3,3-dimethyl-2-butanone, 3-methyl-2-butanone, dioxane, 1,2-dimethoxypropane, methyl ethyl ketone, methyl vinyl ketone, 2-hexanone, 5-methyl-2-hexanone, methyl isoamyl ketone, ethyl butyl ketone, propylene glycol dimethyl ether, propylene glycol methyl ether, nitromethane, nitroethane, 1-nitropropane and 2-nitropropane.

* * * * *